US006700656B1

(12) United States Patent
Chao et al.

(10) Patent No.: US 6,700,656 B1
(45) Date of Patent: Mar. 2, 2004

(54) FLOW VISUALIZATION AND CHARACTERIZATION OF EVAPORATING LIQUID DROPS

(75) Inventors: David F. Chao, North Olmsted, OH (US); Nengli Zhang, North Ridgeville, OH (US)

(73) Assignee: The United States of America as represented by the Administrator of National Aeronautics and Space Administration, Washington, DC (US)

( * ) Notice: Subject to any disclaimer, the term of this patent is extended or adjusted under 35 U.S.C. 154(b) by 57 days.

(21) Appl. No.: 10/252,916

(22) Filed: Sep. 17, 2002

(51) Int. Cl.[7] .............................. G01B 11/26; G01B 9/02
(52) U.S. Cl. ....................................... 356/138; 356/612
(58) Field of Search ................................ 356/138, 601, 356/612, 613, 625, 635, 638; 382/141, 145, 146, 147

(56) References Cited

U.S. PATENT DOCUMENTS

| | | | | |
|---|---|---|---|---|
| 4,688,938 A | * | 8/1987 | Demoulin et al. | 356/154 |
| 5,115,677 A | * | 5/1992 | Martin et al. | 73/64.48 |
| 5,444,529 A | * | 8/1995 | Tateiwa | 356/337 |
| 2002/0176072 A1 | * | 11/2002 | Beseki et al. | 356/128 |

OTHER PUBLICATIONS

"The Spreading of Liquid Droplets on Solid Surfaces" by Dodge, Journal of Colloid and Interface Science, vol. 121, No. 1, Jan. 1988, pp. 154–160.
"A New Method for Contact–Angle Measurements of Sessile Drops" by Ausserre et al, Journal of Colloid and Interface Science, vol. 107, No. 1, Sep. 1985, pp. 5–13.
"Natural Convection in Evaporating Minute Drops" by Zhang et al, Journal of Heat Transfer, vol. 104, Nov. 1982, pp. 656–662.
"Visualization of Evaporative Convection in Minute Drops by Laser Shadowgraphy" by Zhang et al, Rev. Sci. Instrum., vol. 54, No. 1, Jan. 1983, pp. 93–96.
"Visualization of Evaporative Convection in Binary Drops by Laser Shadowgraphy and Holographic Interferometry" by Zhang et al.
"Flow Visualization in Evaporating Liquid Drops and Measurement of Dynamic Contact Angles and Spreading Rate" by Zhang et al, NASA/TM—2001–211284, Nov. 2001, pp. 1–9.
"A New Laser Shadowgraphy Method for Measurements of Dynamic Contact Angle and Simultaneous Flow Visualization in a Sessile Drop" by Zhang et al, Optics and Laser Technology, JOLT 687, published Apr. 2002, 8 pages.

* cited by examiner

*Primary Examiner*—Michael P. Stafira
(74) *Attorney, Agent, or Firm*—Kent N. Stone

(57) ABSTRACT

An optical system, consisting of drop-reflection image, reflection-refracted shadowgraphy and top-view photography, is used to measure the spreading and instant dynamic contact angle of a volatile-liquid drop on a non-transparent substrate. The drop-reflection image and the shadowgraphy is shown by projecting the images of a collimated laser beam partially reflected by the drop and partially passing through the drop onto a screen while the top view photograph is separately viewed by use of a camera video recorder and monitor. For a transparent liquid on a reflective solid surface, thermocapillary convection in the drop, induced by evaporation, can be viewed nonintrusively, and the drop real-time profile data are synchronously recorded by video recording systems. Experimental results obtained from this technique clearly reveal that evaporation and thermocapillary convection greatly affect the spreading process and the characteristics of dynamic contact angle of the drop.

18 Claims, 10 Drawing Sheets

(a) top-view photograph  (b) reflection-refracted shadowgraph

-Typical instant top-view photograph of a silicone oil (50 cSt.) sessile drop and its corresponding reflection-reflected shadowgraph.

-Evolution of drop contact diameter, and contact angle for a silicone oil (50 cSt.) drop of volume 2.2 μl.

- Evolution of drop contact diameter, contact angle, and volume for an n-pentane drop of initial volume 1.65 µl.

-Evolution of drop contact diameter, contact angle, and volume for a freon-113 drop of initial volume 2.41 µl.

FLOW VISUALIZATION AND CHARACTERIZATION OF EVAPORATING LIQUID DROPS

The invention described herein was made by a civil servant employee of the United States Government, and a non-civil servant employee working under a NASA contract, and is subject to the provisions of Section 305 of the National Aeronautics and Space Act of 1958, Public Law 85–568 (72 Stat. 435; 42 U.S.C. 2457).

BACKGROUND OF THE INVENTION

1. Field of the Invention

The invention relates generally to the study, visualization and characterization of liquid drops. More specifically, it relates to a means of accurately determining dynamic contact angles and spreading rates of drops on a non-transparent surface.

2. Discussion of Relevant Art

The spreading of an evaporating liquid on a solid surface occurs in many practical processes, such as coating, painting, gluing, soldering, lubricating, mold filling, and many processes in thermal engineering. The typical processes involving heat transfer are film cooling, boiling, and liquid transportation in heat pipes. Most studies on liquid drop spreading have focused on nonvolatile liquid sessile drops for their simplicity, both in experimental measurements and theoretical analysis. The occurrence of liquid evaporation is, however, inevitable. This evaporation can induce convection in the drop, thought to be attributable to changes in surface tension caused by local variations in the temperature on the surface of the drop. The effect of the convection on the wetting and spreading of the drop is not clear.

A laser-shadowgraphic system has been used to simultaneously visualize the thermocapillary convection inside a volatile drop, and measure the spreading rate of the drop. Unfortunately, this system can only be used on sessile drops spreading on transparent substrates.

Prior techniques have suggested using the reflection of parallel beam on the surface of a sessile drop to measure the contact angle of a drop on a non-transparent substrate. This can work only when the surface of the liquid drop has enough reflectance.

BRIEF DESCRIPTION OF THE INVENTION

The effects of evaporation on the spreading and contact angle of a liquid drop are important for a more complete understanding of these engineering processes and are of more practical interests to research and production personnel.

One object of the present invention is a non-intrusive method and apparatus to characterize the physical attributes of volatile, as well as non-volatile, liquid sessile drops.

Another object is to enable the instantaneous measurement of contact angle and spreading of a liquid drop in any direction.

Yet another object is to permit the determination of the effects of evaporation on the spreading and contact angle of a liquid drop.

Still another object is to enable the flow phenomena in transparent drops on a reflective solid surface to be visualized without the need to use microparticle tracers.

An additional object is to measure instant contact angle and spreading characteristics of a drop in any direction, even if the drop is non-transparent or is on a non-reflective substrate but without visualization of internal flow patterns.

The present invention relates to an apparatus and method of measuring the spreading characteristics of a liquid drop on a non-transparent surface. For a reflective solid surface, such as an aluminized glass plate or any substrate with a smooth surface having enough reflectance, the present invention not only determines the contact angles and spreading characteristics of a liquid drop in any direction simultaneously, but also allows visualization of the fluid flow inside the drop to identify the influences of the flow on the contact angles and spreading of the drop. As for non-reflective, solid surfaces or nontransparent liquid drops, the present invention is useful for measuring the contact angle and spreading characteristics of the drop in any direction, however, without the visualization of flow, if any, within the drop.

A source of white light and a laser beam are collimated. Generally, the collimated beams are partially reflected by the drop surface to form a drop-reflection image and partially pass through the liquid drop to form a reflection-refracted image of the laser beam without obstruction to the top view of the drop. The dynamic contact angle and spreading rate in all directions and the effects of the evaporation on the spreading and the contact angles can then be determined. Typically, the beam of white light and the laser beam are combined via a beam splitter before being collimated. The apparatus includes a second beam splitter through which the collimated beams change direction and are perpendicularly projected on the drop. The beams are partially reflected by the drop surface and partially pass through the drop without obstructing the top view of the drop. The drop-reflection image and the reflection-refracted image pass through a third beam splitter and are projected onto a screen. The apparatus includes means, such as two cameras, video recorders and monitors for recording and viewing the drop-reflection and shadowgraphic images and the magnified top view of the drop.

DETAILED DESCRIPTION OF THE INVENTION

Figure 1:
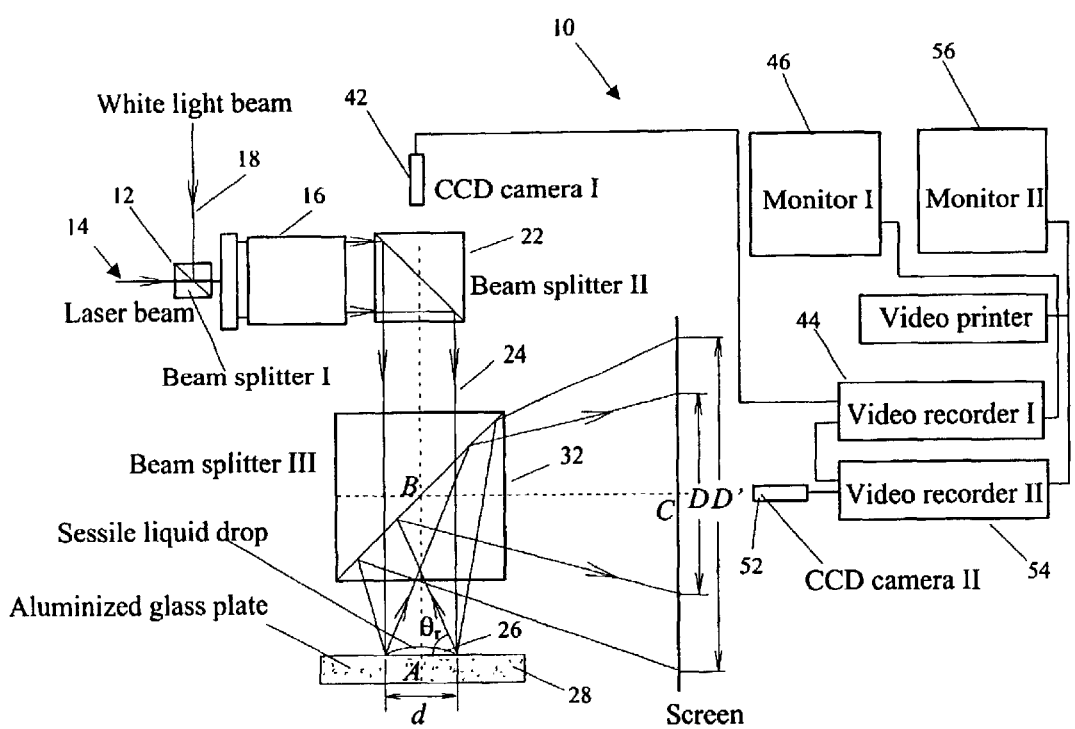
FIG. 1 is a diagram showing the optical system of the present invention using a reflective substrate.

An optical system, which combines drop-reflection image, laser reflection-refracted shadowgraphy and direct magnified top-view photography, is used to visualize inside flow phenomena for a transparent liquid-reflective substrate surface system and to simultaneously measure the spreading and instant dynamic contact angle of a volatile-liquid drop on a nontransparent substrate. The system is also useful for measuring the spreading and instant dynamic contact angle of a volatile-liquid drop on a nontransparent substrate or of a nontransparent liquid drop without the non-intrusive flow visualization. The apparatus consists of a laser light, a white light, a collimator, three beam splitters, two video recording systems, each consisting of a charge-coupled device (CCD) zoom camera, video recorder and monitor, a test plate with a smooth surface, such as aluminized glass plate, and a screen, as illustrated in FIG. 1.

This figure shows an apparatus 10 that is capable of performing a dynamic analysis of the spreading and contact angle characteristics of a sessile drop of liquid on the surface of a non-transparent surface. The apparatus 10 comprises a first beam splitter 12, a second beam splitter 22 and a third beam splitter 32. These beam splitters are optical devices useful for dividing a light beam into two or more paths. They typically employ a prism system and are available from a variety of sources, such as Newport Corporation. A laser beam 14 passes through the first splitter 12 and through an optical collimator 16 to the second beam splitter 22. The laser beam comprises monochromatic light generated by powering a source, such as a Uniphase Model 1105p, 10 mW cylindrical helium neon laser. A beam 18 of white light enters the first splitter 12 at right angles to the laser beam 14. The white light is obtained from a suitable source, such as an Olympus Model Highlight 2000. The collimator, such as a Newport Model LC-075, utilizes a fine slit at the principal focus of a converging lens or mirror. The collimated beams 24 from the collimator pass through the third beam splitter 32 via the second beam splitter 22.

A first CCD camera 42 (with zoom lens) views the image of the white light that outlines the perimeter of the drop. The camera contains a photodiode array whose response to the image of the drop focused on the surface of the array is converted electronically into a video signal that is recorded on a first video recorder 44. The signal is displayed on a first monitor 46. In like manner, a second CCD camera 52 views the drop-reflected and the solid reflection-drop refracted output of the laser beam. The viewed images are recorded on a second video recorder 54 and are displayed on a second monitor 56.

The sessile drop of liquid is placed on a clean substrate surface comprising a non-transparent material, such as an aluminized glass plate (or any substrate with a smooth surface having enough reflectance). The contact surface of the plate must be clean so as to minimize the influences of contaminants on the spread and the evaporation rate of the drop. The simplest cleaning procedure that has been found to be satisfactory for most common volatile liquids is to wash with ethanol followed by wiping with a lens-cleaning tissue. The plate is then shelved in open air, covered by a soft tissue, for at least 24 hours. By this method, the plate surface is free of residual liquid molecules and remains free of impurities from the ambient air.

The test liquid is carefully deposited on the plate by a microsyringe to form a 1.5 to 2.5 $\mu l$ sessile drop. The spreading and the evaporation are considered to start as soon as the microsyringe is detached from the liquid body.

For the transparent liquid-reflective substrate surface system, the reflection-refracted shadowgraphic image can be used. The reflection-refracted shadowgraphic image, combined with the corresponding top view of the test drop, gives comprehensive information of the contact angle of the drop through the measurements of the diameter of the outmost fringe, D, and of the contact diameter of the drop from the top view, d. The contact-angle time-history is determined in the following manner. The shadowgraphic image collected on the screen at a predetermined distance from the substrate surface, s=AB+BC, where A denotes the drop center on the test plate, and B and C are its images on the reflector of Beam splitter III and the screen, is shown in FIG. 1. The rays are refracted out of the drop at an angle $\theta_r$, with the horizon and form the shadowgraphic image with a diameter D on the screen. By a simple geometric relationship, the following equation can be obtained:

$$\tan\theta_r = \frac{s}{(D+d)/2} \quad (1)$$

Figure 2:
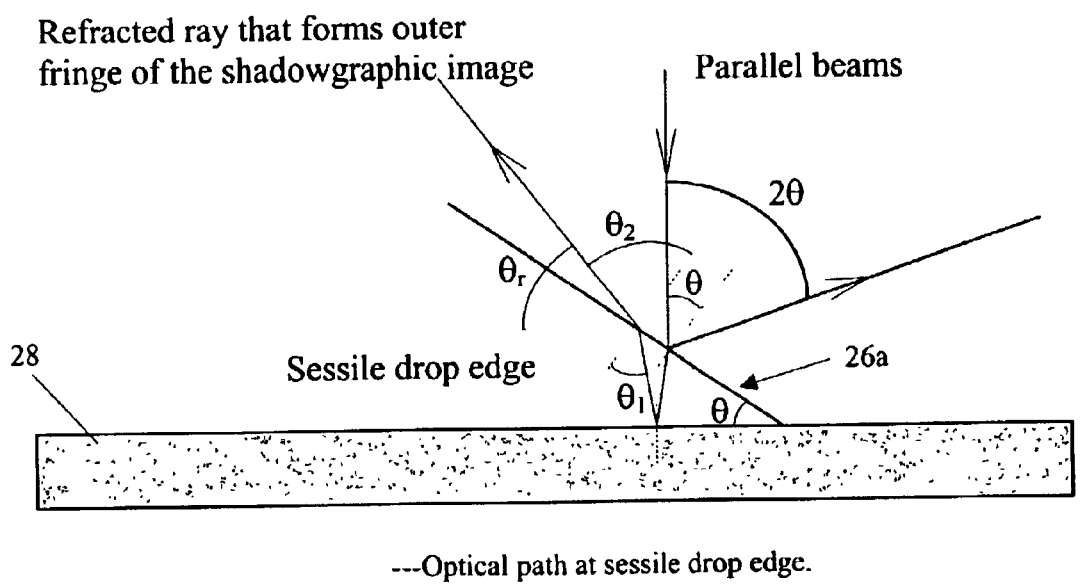
FIG. 2 shows the contact angle of a liquid drop on the flat substrate of FIG. 1.

Both D and d are time dependent because of the spreading and evaporation, and can be accurately measured from the shadowgraphs and the top-view photographs, respectively. To determine the contact angle, $\theta$, consider the detailed optical path near the edge 26a of a drop on a flat reflective plate 28 shown in FIG. 2. Obviously, the angle $\theta_r$ equals $(\pi/2-\theta_2+\theta)$, where $\theta_2$ is the outgoing angle of the ray on the drop surface. Then, Eq. (1) can be rewritten as $$\frac{2s}{D+d} = \frac{\cot\theta_2 + \tan\theta}{1 - \cot\theta_2\tan\theta} \quad (2)$$

Applying Snell's law to each of the air-liquid interfaces and the reflection law to the substrate surface, $\theta_2$ can be related to $\theta$ through the relation $$\sin\theta_2 = n \sin 2\theta \sqrt{1-\sin^2\theta/n^2} - \cos 2\theta \sin\theta \quad (3)$$

where n is the refractive index of the liquid. The contact angle, $\theta$, can be obtained by solving the simultaneous equations (2) and (3).

Based on the sphere-cap approximation, the apex height (h) of the drop can be expressed as:

$$h = \frac{d(1-\cos\theta)}{2\sin\theta} \quad (4)$$

and the volume ($\Omega$) can be expressed as:

$$\Omega = \pi h^2 \left(\frac{d}{2\sin\theta} - \frac{h}{3}\right) \quad (5)$$

The average evaporation rate of the drop, $W_{av}$, is considered an important parameter to measure and can be determined by the equation $$W_{av} = \frac{\Omega_0}{t_f} \quad (6)$$

where $\Omega_0$ is the initial volume of the tested sessile drop and $t_f$ is the lifetime of the drop. The instant evaporation rate of a sessile drop, W, can be calculated by $W = \Delta\Omega/\Delta t$ where $\Delta\Omega$ (t) is the difference in the volume of the drop between the start and end of a given time interval $\Delta t$.

The comprehensive information of a sessile drop, including the local contact angle along the periphery of the drop, the instability of the three-phase contact line, and the deformation of the drop shape, can be obtained and analyzed. Simultaneously, the thermocapillary convection induced by evaporation can also be visualized and, therefore, the effects of the thermocapillary convection on spreading can be investigated. Experimental results obtained by using this unique technique clearly have revealed that thermocapillary convection strongly affects spreading process and the characteristics of dynamic contact angle of the drop.

To further illustrate, but not to limit the present invention and its applicability, the following examples are presented.

EXAMPLE 1

Figure 3:
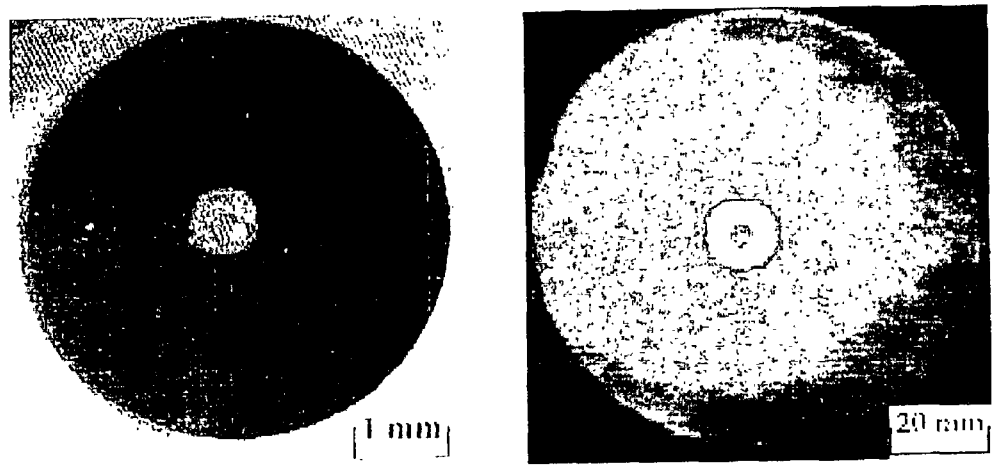
FIGS. 3a and 3b are a photograph and a reflection-refracted shadowgraph of a sessile drop of silicone oil according to the present invention.

A 2.5 µl drop of silicone oil having a viscosity of 50 centistokes was placed on a cleaned aluminized glass plate in open air. The drop is typically dome-shaped. The top view photograph and the reflection-refracted shadowgraph were synchronously recorded and are shown as FIGS. 3a and 3b, respectively. The bright circle at the center of the photograph is formed by reflection of the parallel light beams at the summit of the drop. The contact diameter of the drop can be measured directly from the photograph. As the image of the spreading drop is recorded, the change of the diameter is readily quantified. The contact diameter can also be approximated from the projected image as represented by the dark circle at the center of FIG. 3b. However, this has a greater error because the image is embedded in a substantially larger shadowgraphic image. It will be noted from FIG. 3b that internal convective flow is not present due to the calm spread of the drop caused by its non-volatile nature.

Figure 4:
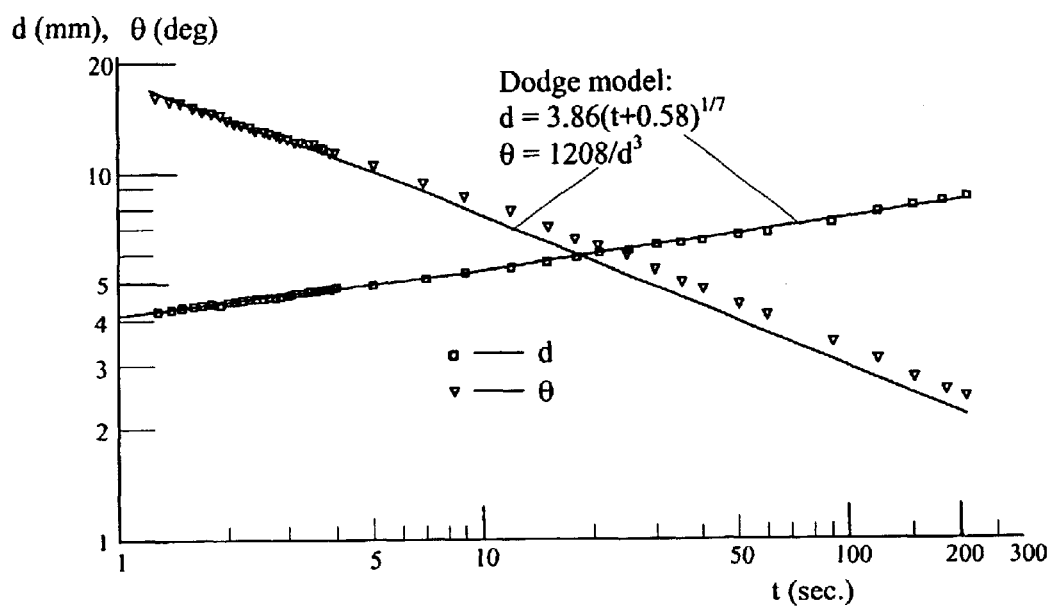
FIG. 4 is a plot of drop contact diameter and contact angle characteristics for the drop of silicone oil measured and calculated from its instant magnified top view photographs and shadowgraphs, typical ones of which are shown in FIGS. 3a and 3b.

As shown in FIG. 4, the relationship of the contact diameter and the contact angle is linear. Because of the non-volatility of the oil, the volume of the drop remains constant during the entire time span of the measurements. For the silicone oil drops, the drop spreading follows Dodge's relation, $d = k(t+a)^{1/7}$, that depicts the spreading law of a nonvolatile drop.

However, the spreading characteristics of a volatile drop are quite different from those of a nonvolatile drop, such as silicone oil. Generally, after a short initial spreading period, the volatile drop maintains approximately a constant contact-diameter for a brief period, the so-called spreading-evaporation balance stage, followed by a monotonic contraction, referred to as the evaporation-dominant contraction stage.

EXAMPLE 2

Figure 5:
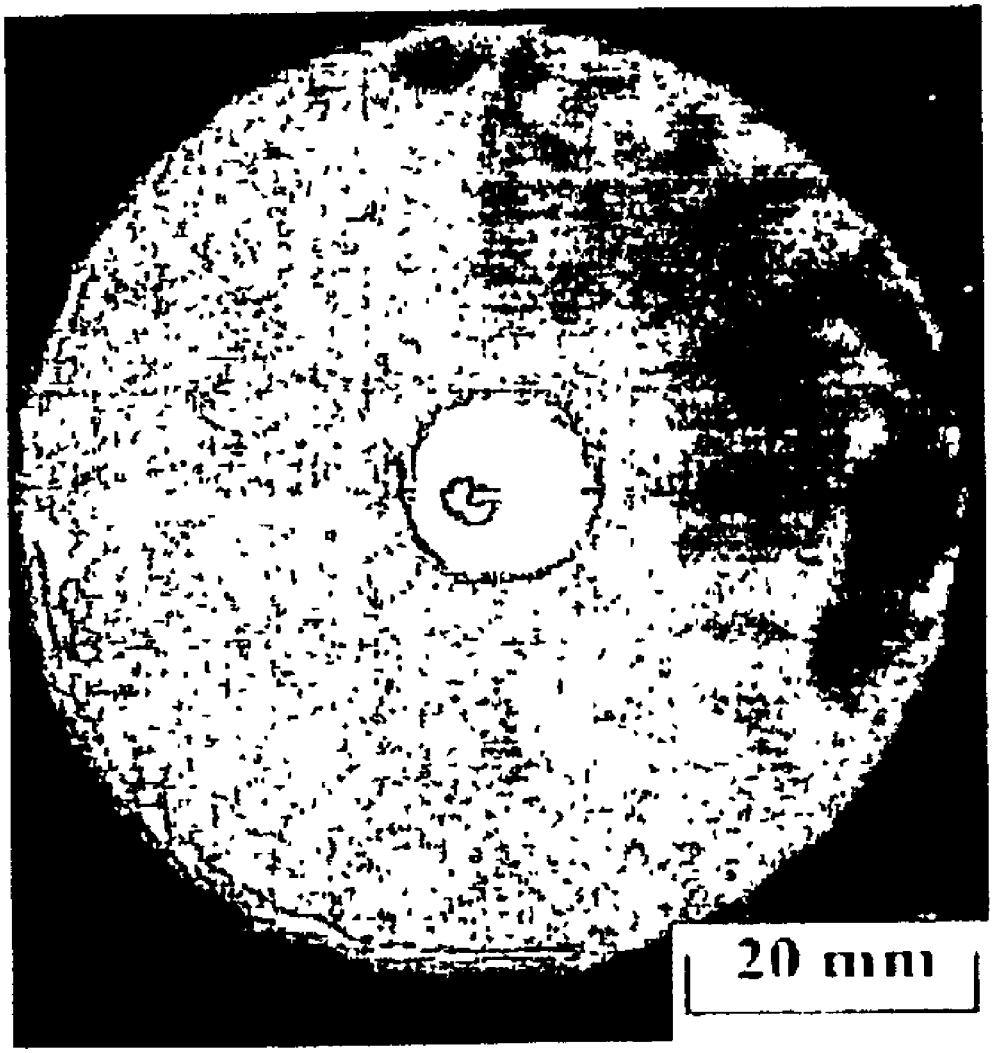
FIG. 5 is a shadowgraph of a sessile drop of n-pentane on a non-transparent plate.
Figure 6:
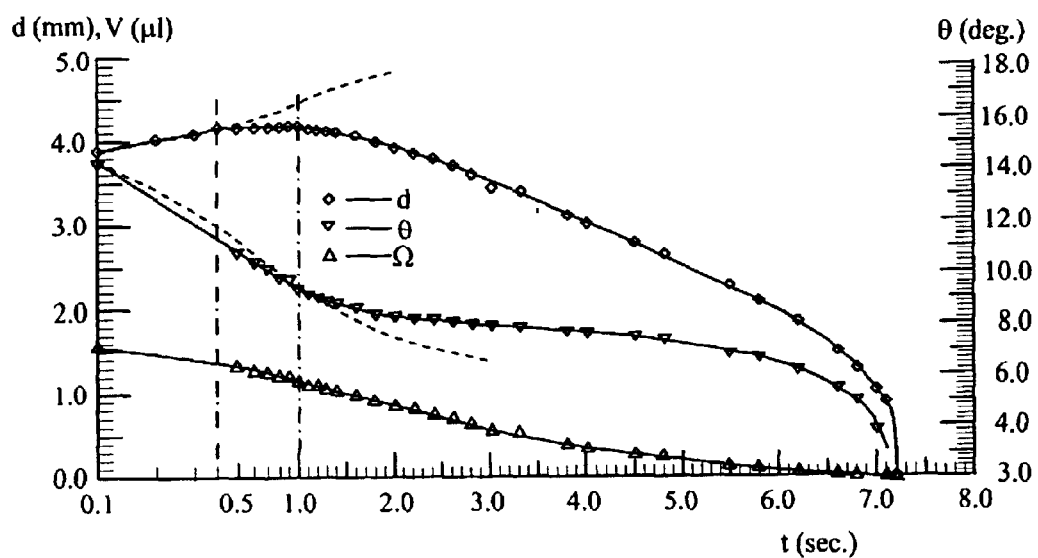
FIG. 6 is a graph showing the drop volume, contact angle and contact diameter of the drop of n-pentane measured and calculated from its instant top views and shadowgraphs. Typical shadowgraph of the drop is shown in FIG. 5.

To better understand the use of the present invention in characterizing the flow characteristics of a volatile liquid, a drop of n-pentane having an initial volume of 1.65 µl is placed on an aluminized plate cleaned as before. The spreading of an n-pentane drop deviates from the Dodge relation after the short initial spreading period and further in time, especially after the thermocapillary convection occurs when the spreading-evaporation balance stage ends. The reflection-refracted shadowgraph of this drop is shown in FIG. 5. Evolutions of contact diameter, contact angle and volume for an n-pentane drop with an initial volume of 1.65 µl are plotted in FIG. 6.

EXAMPLE 3

Figure 7:
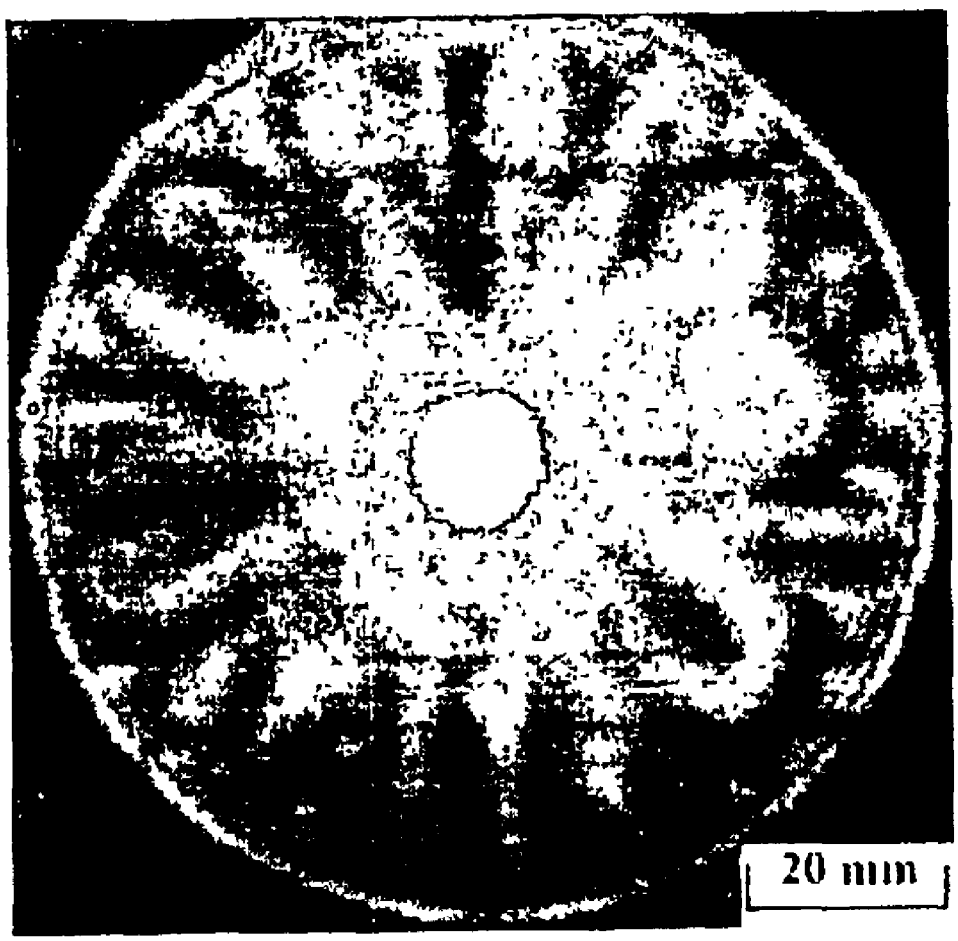
FIG. 7 is a shadowgraph of a sessile drop of Freon-113 on a non-transparent plate.
Figure 8:
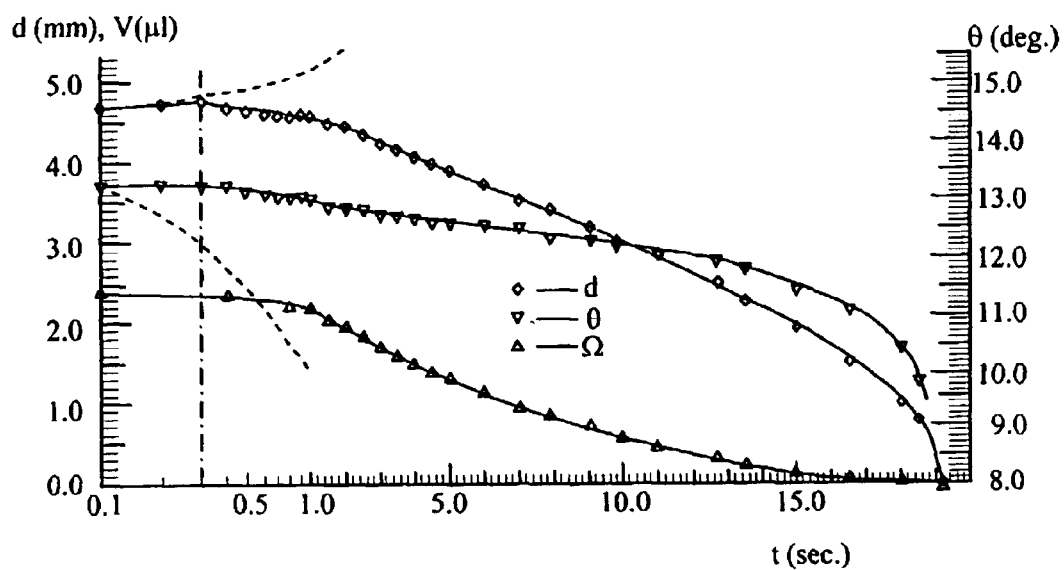
FIG. 8 is a graph showing the drop volume, contact angle and contact diameter of the drop of Freon-113 measured and calculated from its instant magnified top view photographs and shadowgraphs. Typical shadowgraph of the drop is shown in FIG. 7.
Figure 9:
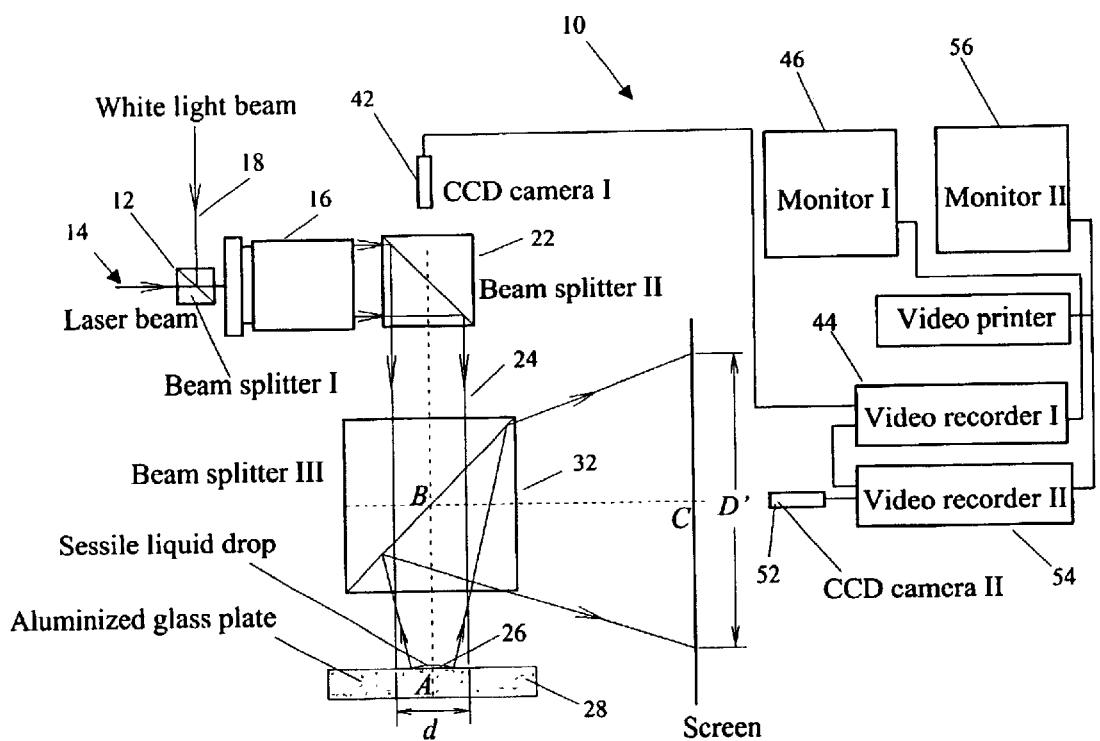
FIG. 9 is a diagram showing the optical system for a nontransparent drop or on a non reflective substrate.
Figure 10:
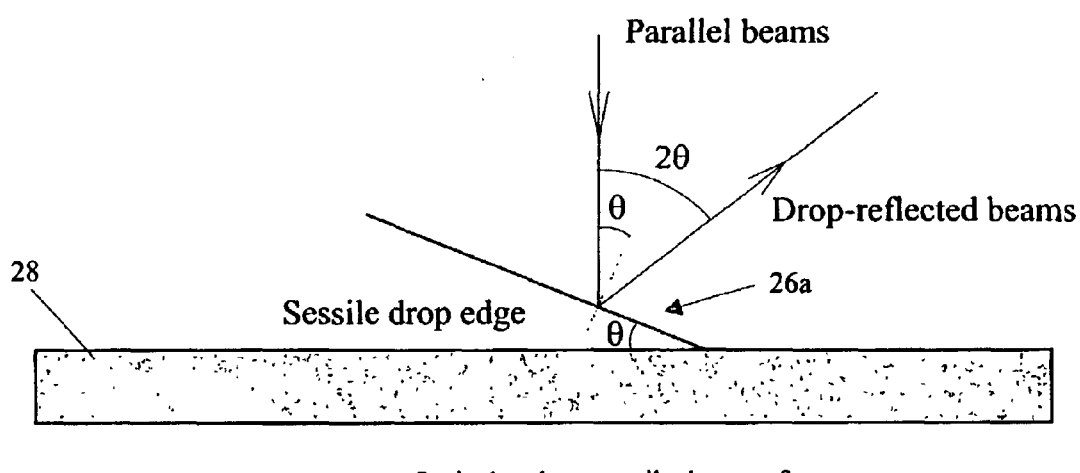
FIG. 10 shows the contact angle of a liquid drop of the flat substrate of FIG. 9.

A drop of Freon-113 having an initial volume of 2.41 µl is placed on an aluminized plate cleaned as in the previous examples. Typical instant reflection-reftacted shadowgraph is shown in FIG. 7. Although the evaporation rate of the Freon-113 sessile drop, $W_{av} = 0.126$ µl/sec, is lower than that of an n-pentane sessile drop, ($W_{av} = 0.229$ µl/sec), the initial spreading stage of a Freon-113 drop is much shorter than that of an n-pentane drop. Additionally, no spreading-evaporation balance-stage is observed, as shown in FIG. 8. The spreading of the Freon-113 drop deviates from Dodge's relation as depicted by the dish line from the very beginning because thermocapillary convection induced by evaporation has occurred.

For the non-reflective substrate surface or nontransparent liquid systems, no reflection-refracted shadowgraph is available. However, the drop-reflected image can be used. The following simple equation directly gives the contact angle:

$$\theta = \frac{1}{2}\arctan\frac{D' - d}{2s} \quad (7)$$

The apex height of the drop, h, the drop volume, $\Omega$, and the average evaporation rate of the drop, $W_{av}$, can be calculated using equations (4), (5), and (6), respectively.

Among the advantages of the present invention are the following:

1. Because of non-transparency of the substrate and the spherical cap shape of the sessile drop, reflection-refracted shadowgraphy is a unique method to study the effects of thermocapillary convection on the spreading of volatile drops.

2. The instantaneous drop size, including the contact diameter, contact angle, and drop volume can be accurately determined through the top-view photograph of the drop and its corresponding shadowgraphic image, which are synchronously recorded.

3. The comprehensive information of an evaporating drop on a non-transparent substrate, including the local contact angle along the periphery of the drop, the instability of the three-phase contact line, and the deformation of the drop shape, can be obtained and analyzed.

4. The effects of thermocapillary convective flow, induced by evaporation, on the spreading of volatile drops can be accurately investigated for the transparent liquid-reflective solid surface systems.

5. Both transparent liquid-reflective solid surface systems and non-reflective solid surface or non-transparent liquid systems can be tested using the same apparatus based on the present invention.

Although the invention has been described in terms of using three beam splitters, two video recorders and two monitors, it is within the scope of the invention that the functions of these devices can be performed by other comparable devices and, in some instances, may be combined or consolidated in accordance with evolving technology. While the invention has been described in combination with embodiments thereof, it is evident that many alternatives, modifications, and variations will be apparent to those skilled in the art in light of the foregoing teachings.

Accordingly, the invention is intended to embrace all such alternatives, modifications and variations as fall within the spirit and scope of the appended claims.

What is claimed is:

1. A method for characterizing the spreading properties of a liquid drop on a non-transparent substrate, comprising the steps of:
    a) collimating a beam of white light and a laser beam into parallel beams;
    b) reflecting at least a part of the collimated light beam from the surface of the liquid drop to form a drop reflection image;
    c) displaying the drop reflection image, and
    d) simultaneously displaying an image of the top view of the drop.

2. The method according to claim 1 wherein the drop is transparent, the substrate is reflective, and a laser reflection-refracted shadowgraph image of the drop is displayed simultaneously with the display of the drop reflection image.

3. The method according to claim 1 wherein the drop is not transparent and the light beam is fully reflected from the surface of the drop.

4. The method according to claim 1 wherein the drop is at least partially transparent, the substrate is non-reflective, and the beam is reflected from the surface of the drop.

5. The method according to claim 1 wherein the characterization includes the determination of dynamic contact angle and the measurement of the spreading rate.

6. The method according to claim 1 wherein the beam of white light and the laser beam converge on a first beam splitter before being collimated.

7. The method according to claim 5 wherein the parallel beams are reflected by a second beam splitter to change direction from horizontal to perpendicular before passing through a third beam splitter onto the drop.

8. The method according to claim 7 wherein the drop-reflection image and the reflection-refracted image are reflected and projected onto a screen by a third beam splitter.

9. The method according to claim 1 wherein the spreading characteristics to be measured are drop contact angle and the spreading rate.

10. The method according to claim 1 wherein the non-transparent substrate surface may be reflective or non-reflective.

11. The method according to claim 1 wherein the drop-reflection image and the reflection-refracted image of the laser beam are viewed by a video camera and are displayed on a first monitor and the photograph of the top of the drop is viewed by a second video camera and is displayed on a second monitor.

12. An optical system for viewing the spreading characteristics of a liquid drop on a non-transparent surface, comprising:
    a) a source for generating a laser beam;
    b) a source for generating a beam of white light;
    c) a collimator for converting the laser beam and the beam of white light into parallel beams;
    d) means for directing the collimated beams on the liquid drop to produce a drop-reflection image and a reflection-refracted image of the laser beam and a photograph of the top view of the drop, and
    e) means for simultaneously displaying the drop-reflection image and the reflection-refracted image and the photographic image of the top view of the drop.

13. The system according to claim 12 wherein the non-transparent surface is any kind of substrate including the substrates with a smooth reflective surface and the substrates with a smooth or non-smooth, non-reflective surface.

14. The system according to claim 12 further including a second splitter for directing parallel beams perpendicularly to the non-transparent surface.

15. The system according to claim 14 further including a third beam splitter to project the drop-reflection image and the reflection-refracted image of the laser beam onto a screen.

16. The system according to claim 14 further including a first camera, a first video recorder and a first monitor for recording and viewing the visual image of the laser beam on the screen.

17. The system according to claim 16 further including a second camera, a second video recorder and a second monitor for recording and viewing the photographic image of the drop.

18. The system according to claim 12 wherein the source of the laser beam is a helium-neon laser.

* * * * *